United States Patent [19]

Guindon et al.

[11] Patent Number: 5,071,835
[45] Date of Patent: Dec. 10, 1991

[54] RIBONUCLEOTIDE REDUCTASE INHIBITORS

[75] Inventors: Yvan Guindon, Montreal; Pierre Lavalee, Rosemere; Sumanas Rakhit, Dollard des Ormeaux; Gregory P. Cosentino, Montreal, all of Canada

[73] Assignee: Bio-Mega Inc., Laval, Canada

[21] Appl. No.: 474,589

[22] Filed: Feb. 1, 1990

[30] Foreign Application Priority Data

Feb. 17, 1989 [CA] Canada .................................. 591372

[51] Int. Cl.$^5$ .......................... C07K 7/00; C07K 7/08; A61K 37/02
[52] U.S. Cl. ........................................ 514/13; 514/15; 514/17; 514/18; 514/19; 530/326; 530/327; 530/328; 530/329
[58] Field of Search ...................... 514/13, 15, 17, 18, 514/19; 530/326, 327, 328, 329

[56] References Cited

U.S. PATENT DOCUMENTS

| | | | |
|---|---|---|---|
| 4,448,730 | 5/1984 | van't Riet | 260/500.5 |
| 4,795,740 | 1/1989 | Cohen et al. | 514/14 |
| 4,814,432 | 3/1989 | Freidinger et al. | 530/329 |
| 4,837,304 | 6/1989 | Garskey et al. | 530/328 |
| 4,845,195 | 7/1989 | Colonno et al. | 530/330 |

OTHER PUBLICATIONS

Thelander et al., Molecular and Cellular Biology, vol. 6, No. 10, 1986, pp. 3433–3442.
van'Reit et al., "Synthesis of Hydroxy-and Amino--Substituted Benzohydroxamic Acids: Inhibition of Ribonucleotide Reductanse and Antitumor Activity", J. Med. Chem. 22 (5):589 (1979).
Takeda et al., "Role Ribonucleotide Reductase in Expression of the Neoplastic Program", Life Sciences 28:1007 (1981).
Weber et al., "Dynamics of Modulation of Biochemical Programs in Cancer Cells", Adv. Enz. Reg. 19:87 (1981).
Cory et al., "Specific Inhibition of Subunits of Ribonucleotide Reductase as a New Approach to Combination Chemotherapy", Adv. Enz. Reg. 19:139 (1981).

*Primary Examiner*—Lester L. Lee
*Assistant Examiner*—Avis Davenport
*Attorney, Agent, or Firm*—David E. Frankhouser; Daniel Reitenbach; Mary-Ellen M. Timbers

[57] ABSTRACT

Disclosed herein are peptides of the formula

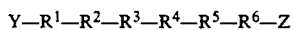

$$Y-R^1-R^2-R^3-R^4-R^5-R^6-Z$$

wherein $R^1$ to $R^5$ are designated amino acid residues; $R^6$ is Phe, homoPhe or an amino acid residue derived from 2-amino-3-cyclohexylpropionic acid, 2-amino-3-(4-(lower alkoxy)phenyl) propionic acid or 2-amino-3-(4-halophenyl)propionic acid; Y is Phe, desamino-Phe, (lower alkanoyl)-Phe, p-haloPhe, Tyr, desamino-Tyr or (lower alkanoyl)-Tyr, or Y is the decapeptide radical W—Val—$R^7$—Ser—$R^8$—$R^9$—Thr—Glu—$R^{10}$—Ser—Phe wherein W is hydrogen or lower alkanoyl and $R^7$ to $R^{10}$ are designated amino acids residues, or Y is a fragment of the decapeptide radical wherein from one to nine of the amino acid residues (i.e. Val to Ser) may be deleted serially from the amino terminus of the decapeptide radical; and Z is hydroxy, amino, lower alkylamino or di(lower alkyl)amino. The peptides inhibit mammalian ribonucleotide reductase and are indicated for preventing or ameliorating abnormal cell proliferation.

11 Claims, No Drawings

RIBONUCLEOTIDE REDUCTASE INHIBITORS

FIELD OF THE INVENTION

This invention relates to peptides possessing selective ribonucleotide reductase inhibiting properties, to processes for their production, to pharmaceutical compositions of the peptides, and to the use of the peptides to inhibit ribonucleotide reductase.

BACKGROUND OF THE INVENTION

Ribonucleotide reductase (RR) is the enzyme responsible for the reductive conversion of ribonucleotides to deoxyribonucleotides. The latter conversion is the rate controlling step in the biosynthesis of deoxyribonucleic acid (DNA), an essential principle for cell replication. RR activity has been linked directly to the proliferation of normal and neoplastic cells, with significantly higher levels of RR activity being found in neoplastic cells (see E. Takeda and G. Weber, Life Sciences, 28, 1007 (1981) and G. Weber et al., Adv. Enz. Reg., 19, 87 (1981). Hence, the inhibition of RR activity is a valid target in the search for agents which will prevent or ameliorate abnormal cell proliferation as occurs, for example, in neoplasia and psoriasis.

Several inhibitors of mammalian RR have been investigated as potential antineoplastic agents or antitumor agents; for example, see B. van't Riet et al., J. Med. Chem., 22, 589 (1979), J. G. Cory et al., Adv. Enz. Reg., 19, 139 (1981), and B. van't Riet et al., U.S. Pat. No. 4,448,730, issued May 15, 1984. However, none have proved to be entirely satisfactory in clinical trials and only one RR inhibitor, hydroxyurea, is available to the physician for use as an antineoplastic agent. The latter drug, nevertheless, finds limited use because of side-effects and because frequent and large doses are required to maintain an effective concentration of the drug in vivo (see Van't Riet et al., J. Med. Chem., supra). Accordingly, there is a need for an effective and safe inhibitor of mammalian RR.

The present application discloses a new group of peptides which are potent inhibitors of mammalian RR. This attribute, together with a relative lack of toxicity, renders the peptides useful as agents for combatting disease states associated with abnormal cell proliferation.

Peptides have previously been reported to be inhibitors of RR, see for instance J. H. Subak-Sharpe et al., UK patent application 2185024, published July 8, 1987, E. A. Cohen et al., European patent application 246630, published Nov. 25, 1987, and R. Freidinger et al., European patent application 292255, published Nov. 23, 1988. However, unlike the present peptides, the previously reported peptides are inhibitors of a viral RR and not mammalian RR.

SUMMARY OF THE INVENTION

The peptides of this invention are represented by formula 1

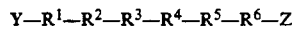

Y—R$^1$—R$^2$—R$^3$—R$^4$—R$^5$—R$^6$—Z    1 wherein

R$^1$ is Thr, Thr(OBzl), Ser, Leu, Ile, Val, N-Me-Val or Ala,

R$^2$ is Leu, D-Leu, N-Me-Leu, Ile, Val, Ala, Cha, N-Me-Cha or Phe,

R$^3$ is Asp, D-Asp, N-Me-Asp, Asp(NMe$_2$), Asn, Glu, Gln, Leu, Ile, Val, Ala, Gly or Phe,

R$^4$ is Ala, D-Ala, Val, Ile, Leu, Asp or Glu,

R$^5$ is Asp, D-Asp, N-Me-Asp, Glu, D-Glu or N-Me-Glu,

R$^6$ is Phe, homoPhe, or a divalent amino acid residue of formula X—CH$_2$CH(NH—)CO— wherein X is cyclohexyl, 4-(lower alkoxy)phenyl or 4-halophenyl;

Y is Phe, desamino-Phe, (lower alkanoyl)-Phe, p-haloPhe, (lower alkanoyl)-p-haloPhe, Tyr, desamino-Tyr or (lower alkanoyl)-Tyr, or Y is the decapeptide radical W-Val-R$^7$-Ser-R$^8$-R$^9$-Thr-Glu-R$^{10}$-Ser-Phe wherein W is hydrogen or lower alkanoyl, and R$^7$ is Met or Ile, R$^8$ is Ser or Asn, R$^9$ is Pro or Ser, and R$^{10}$ is Asn, Gln, or Y is a fragment of said decapeptide radical wherein W, R$^7$, R$^8$, R$^9$ and R$^{10}$ are as defined hereinabove and wherein from one to nine of the amino acid residues (i.e. Val to Ser) may be deleted serially from the amino terminus of the decapeptide radical; and Z is hydroxy, amino, lower alkylamino or di(lower alkyl)amino; or a therapeutically acceptable salt thereof.

A preferred group of the peptides is represented by formula 1 wherein R$^1$ to R$^6$, inclusive, are as defined hereinabove, Y is Phe, desamino Phe, AcPhe, Ac-p-haloPhe, Tyr, desamino-Tyr or AcTyr, and Z is hydroxy or amino; or a therapeutically acceptable salt thereof.

Another preferred group of the peptides is represented by formula 1 wherein R$^1$ to R$^6$, inclusive, are as defined hereinabove, Y is the decapeptide radical or a fragment of the decapeptide radical, as defined hereinabove, and Z is hydroxy or amino; or a therapeutically acceptable salt thereof.

A more preferred group of the peptides is represented by formula 1 wherein R$^1$ is Thr, Thr(OBzl), Ser, Ile, Val, N-Me-Val or Ala, R$^2$ is Leu, N-Me-Leu, Ile, Val or N-Me-Cha, R$^3$ is Asp, Asp(NMe$_2$), Asn, Glu, Gln or Ala, R$^4$ is Ala, Val, Asp or Glu, R$^5$ is Asp, N-Me-Asp or Glu, R$^6$ is Phe, homoPhe, or a divalent residue of formula X—CH$_2$CH(NH—)CO— wherein X is cyclohexyl, 4-methoxy phenyl or 4-fluorophenyl, Y is Phe, desamino-Phe, AcPhe, Ac-p-IPhe, Tyr, desamino-Tyr or AcTyr, and Z is hydroxy or amino; or a therapeutically acceptable salt thereof.

Another more preferred group of the peptides is represented by formula 1 wherein R$^1$ to R$^6$, inclusive, are as defined in the last instance, Y is the aforementioned decapeptide radical or the aforementioned fragment of the decapeptide radical wherein W is hydrogen or acetyl and R$^7$ to R$^{10}$, inclusive, are as defined hereinabove, and Z is hydroxy or amino; or a therapeutically acceptable salt thereof.

A most preferred group of the peptides is represented by formula 1 wherein R$^1$ is as defined in the last instance, R$^2$ is Leu, N—Me-Leu or N-Me-Cha, R$^3$ is Asp, Asp(N-Me$_2$), Asn, Gln or Ala, R$^4$ is Ala or Glu, R$^5$ is Asp or N-Me-Asp, R$^6$ is Phe, Y is Phe, desamino-Phe or AcPhe, and Z is hydroxy; or a therapeutically acceptable salt thereof.

Another most preferred group of the peptides is represented by formula 1 wherein R$^1$ to R$^6$, inclusive, are as defined in the last instance, Y is the aforementioned decapeptide radical or an aforementioned fragment of the decapeptide radical wherein W is hydrogen or acetyl, $R^7$ is Met or Ile, $R^8$ is Ser or Asn, $R^9$ is Pro or Ser, and $R^{10}$ is Asn, and Z is hydroxy; or a therapeutically acceptable salt thereof.

Included within the scope of this invention is a pharmaceutical composition for treating abnormal cell proliferation in a mammal, comprising a peptide of formula 1, or a therapeutically acceptable salt thereof, and a pharmaceutically or veterinarily acceptable carrier.

Within the scope of this invention a method is included for preventing or ameliorating abnormal cell proliferation in a mammal which comprises administering to the mammal an effective amount of a peptide of formula 1, or a therapeutically acceptable salt thereof.

Also included within the scope of the invention is a method of inhibiting ribonucleotide reductase which comprises administering to a mammal carrying a tumor having a relatively high ribonucleotide reductase level of activity, an amount of a peptide of formula 1, or a therapeutically acceptable salt thereof, effective to inhibit ribonucleotide reductase.

Processes for preparing the peptides of formula 1 are described hereinafter.

DETAILS OF THE INVENTION

General

The term "residue" with reference to an amino acid means a radical derived form the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commission of Biochemical Nomenclature, see European Journal of Biochemistry, 138, 9 (1984). For instance, Met, Met(O), Val, Thr, Glu, Gln, Ala, Ile, Asp, Phe, Ser, Leu, Asn and Tyr represent the residues of L-methionine, L-methionine sulfoxide, L-valine, L-threonine, L-glutamic acid, L-glutamine, L-alanine, L-isoleucine, L-aspartic acid, L-phenylalanine, L-serine, L-leucine, L-asparagine and L-tyrosine, respectively.

The symbol "Ac", when used herein as a prefix to a three letter symbol for an amino acid residue, denotes the N-acetyl derivative of the amino acid; for example, "AcPhe" represents the residue of N-acetyl-L-phenylalanine. Likewise, the symbol "N-Me", when used herein as a prefix to a three letter symbol for an amino acid residue, denotes the N-methyl derivative of the amino acid; for example, N-Me-Val represents the residue of N-methyl-L-valine. The term "desamino", when used as a prefix denotes an amino acid residue wherein the $N^\alpha$-amino group has been replaced with a hydrogen; for example, "desamino-Phe" represents 3-phenylpropanoyl.

Other symbols used herein are:

Thr(OBzl) for the residue of $O^3$-benzyl-L-serine

Asp(NMe₂) for the residue of $N^4$, $N^4$-dimethyl L-asparagine

HomoPhe for the residue of L-homophenylalanine, i.e. 2(S)-amino-4-phenylbutanoic acid Cha for the residue of 2(S)-amino-3-cyclohexyl-propanoic acid p-haloPhe and p-IPhe for the residues of 2(S)-amino-3-(4-halophenyl)propanoic acid and 2(S)-amino-3-(4-iodophenyl)propanoic acid, respectively The amino acid residues, of which the designation therefor is not preceded by "D-", possess the L-configuration, including those with prefixes such as lower alkanoyl and acetyl. The same consideration applies to the divalent amino acid residue "X-CH₂CH—(NH—)-CO—" which also possesses the L-configuration. The amino acid residues of which the designation is preceded by "D-" possess the D-configuration. The starting materials for providing the amino acid residues, usually the corresponding $N^\alpha$-protected amino acids, are commercially available or can be prepared by conventional methods.

The term "halo" as used herein means a halo radical selected from bromo, chloro, fluoro or iodo.

The term "lower alkanoyl" means an alkanoyl group containing two to six carbon atoms and includes acetyl, 1-oxopropyl, 2-methyl-1-oxopropyl, 1-oxohexyl and the like. Similarly, "lower alkanoic acid" means an alkanoic acid of two to six carbon atoms; for example, acetic acid, propionic acid and 3-methylbutyric acid.

The term "lower alkoxy" as used herein means straight chain alkoxy radicals containing one to six carbon atoms and branched chain alkoxy radicals containing three to six carbon atoms and includes methoxy, ethoxy, propoxy, 1-methylethoxy, butoxy and 2,2-dimethylpropoxy.

The term "amino" as used herein means an amino radical of formula —NH₂. The term "lower alkylamino" as used herein means alkylamino radicals containing one to three carbon atoms and includes methylamino, ethylamino, propylamino and 1-methylethylamino. The term "di(lower alkyl)amino" means an amino radical having two lower alkyl substituents each of which contains one to three carbon atoms and includes dimethylamino, diethylamino, ethylmethylamino and the like.

The term "pharmaceutically acceptable carrier" as used herein means a non-toxic, generally inert vehicle for the active ingredient, which does not adversely affect the ingredient.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "coupling agent" as used herein means an agent capable of effecting the dehydrative coupling of an amino acid or peptide free carboxy group with a free amino group of another amino acid or peptide to form an amide bond between the reactants. The agents promote or facilitate the dehydrative coupling by activating the carboxy group. Descriptions of such coupling agents and activated groups are included in general textbooks of peptide chemistry; for instance, E. Schröder and K. L. Lübke, "The Peptides", Vol. 1, Academic Press, New York, N.Y., 1965, pp 2–128, and K. D. Kopple, "Peptides an Amino acids", W. A. Benjamin, Inc., New York, N.Y., 1966, pp 33–51. Examples of coupling agents are thionyl chloride, diphenylphosphoryl azide, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(dimethylamino)phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

Process

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schröder and K. Lübke, cited above, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, IL, U.S.A., 1984.

A common feature of the aforementioned processes for the peptides is the protection of the labile side chain groups of the various amino acid residues with suitable protective groups which will prevent a chemical reaction from occurring at that site until the protective group is ultimately removed. Usually also common feature is the protection of an $\alpha$-amino group on an amino acid or a fragment while that entity reacts at the carboxy group, followed by the selective removal of the $\alpha$-amino protective group to allow subsequent reaction to take place at that location. Usually another common feature is the initial protection of the C-terminal carboxyl of the amino acid residue or peptide fragment, which is to become the C-terminal function of the peptide, with a suitable protective group which will prevent a chemical reaction from occurring at that site until the protective group is removed after the desired sequence of the peptide has been assembled.

Hence, the peptides of formula 1 can be prepared by a process comprising the stepwise coupling, in the order of the amino sequence of the peptide, of the appropriate amino acid residues or peptide fragments (with side chain functional groups duly protected, and with the C-terminal carboxyl of the amino acid residue or peptide fragment, which is to become the C-terminal function of the peptide, duly protected by a C-terminal carboxyl protecting group), in the presence of a coupling agent, to obtain the protected peptide of formula 2

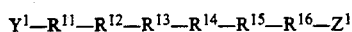

$$Y^1-R^{11}-R^{12}-R^{13}-R^{14}-R^{15}-R^{16}-Z^1 \qquad 2$$

wherein $R^{11}$ is Thr($V^1$), Ser($V^1$), Leu, Val, N-Me-Val or Ala wherein $V^1$ is a protective group for the hydroxyl of Thr or Ser, $R^{12}$ has the same meaning as defined hereinabove for $R^2$, $R^{13}$ is Asp($V^2$), D-Asp($V^2$), N-Me-Asp($V^2$), Asp(NMe$_2$), Asn, Glu($V^2$), Gln, Leu, Ile, Val, Gly or Phe wherein $V^2$ is a protective group for the $\omega$-carboxyl of the amino acid residue designated therewith, $R^{14}$ is Ala, D-Ala, Val, Ile, Leu, Asp($V^2$), or Glu($V^2$) wherein $V^2$ is as defined hereinabove, $R^{15}$ is Asp($V^2$), D-Asp($V^2$), N-Me-Asp($V^2$), Glu($V^2$), D-Glu($V^2$) or N-Me-Glu($V^2$) wherein $V^2$ is as defined hereinabove, $R^{16}$ has the same meaning as defined hereinabove for $R^6$, $Y^1$ is U-Phe, desamino-Phe, (lower alkanoyl)Phe, U-p-haloPhe, (lower alkanoyl)-p-haloPhe, U-Tyr($V^3$), desamino-Tyr($V^3$) or (lower alkanoyl)-Tyr($V^3$) wherein U is an $\alpha$-amino protective group and $V^3$ is a protective group for the hydroxyl of Tyr, or $Y^1$ is the decapeptide radical $W^1$-Val-$R^{17}$-Ser($V^1$)-$R^{18}$-$R^{19}$-Thr($V^1$)-Glu($V^2$)-$R^{20}$-Ser($V^1$)-Phe wherein $V^1$ and $V^2$ are as defined hereinabove, $W^1$ is an $\alpha$-amino protective group or lower alkanoyl, $R^{17}$ is Met, Met(O) or Ile, $R^{18}$ is Ser($V^1$) or Asn wherein $V^1$ is as defined hereinabove, $R^{19}$ is Pro or Ser($V^1$) wherein $V^1$ is as defined hereinabove and $R^{20}$ is Asn or Gln, or $Y^1$ is a fragment of the last-named decapeptide radical wherein $W^1$, $R^{17}$, $R^{18}$, $R^{19}$ and $R^{20}$ are as defined hereinabove and wherein from one to nine of the amino acid residues [i.e. Val to Ser ($V^1$)] may be deleted serially from the amino terminus of the last-named decapeptide radical, and $Z^1$ is a classical carboxyl protective group or a resin support; followed by deprotecting (including cleaving the resin support if present), and acylating and/or amidating if required, the protected peptide of formula 2 to obtain the corresponding peptide of formula 1; and if desired, transforming the peptide of formula 1 into a therapeutically acceptable salt.

The term "resin support", as used herein with reference to $Y^1$, means the radical derived from a solid resin support of the type used in solid phase peptide synthesis. Such resin supports include the well known chloromethylated resins and benzhydrylamine resins, as well as resins which provide a spacer unit between the resin and the first amino acid building block of a peptide-resin system so that after the peptide portion is assembled the resin can be cleaved selectively from the system. Examples of resins with spacers incorporated therein are $\alpha$-(phenylacetamido)benzyl resin (PAB resin), described by E. Giralt et al., Tetrahedron 37, 2007 (1981), and 4-(2-bromo- or 4-(2-chloro-propionyl)phenoxyacetyl BHA resins, photolabile resins described by D. Bellof and M. Mutter, Chemia, 39, 317 (1985).

Examples of side chain protective groups are benzyl for the protective group ($V^1$) for the hydroxyl of Thr or Ser; benzyl, 2,6-dichlorobenzyl or preferably cyclohexyl for the protective group ($V^2$) for the $\omega$-carboxy of Asp or Glu and their related derivatives, and benzyl or preferably 2,6-dichlorobenzyl for the protective group ($V^3$) for the hydroxyl or Tyr. Note that when $R^{11}$ of the protected peptide of formula 2 is Thr(OBzl) the benzyl group can serve a dual role, i.e. serve as the progenitor for the corresponding radical in the ultimate product of formula 1 wherein $R^1$ is Thr(OBzl) or serve as a protective group. When the benzyl group is used as a progenitor, protective groups of the protected peptide of formula 2, if present, are those which can be removed selectively in the presence of benzyl by known methods.

Examples of C-terminal carboxyl protecting group include the classical groups, for example, benzyloxy and 4-nitrophenoxy, and for the present processes include also a "resin support".

In an embodiment of the exclusively solid phase method, the preparation of a peptide of formula 1 in which Z is hydroxy is commenced by coupling the first amino acid relative to the carboxy terminus (the amino acid having an $\alpha$-amino protective group and, if required, a side chain protective group) with PAB resin in the presence of potassium fluoride or cesium chloride to give the corresponding solid resin support having the first amino acid (in protected form) linked thereto. The next step is the removal of the $\alpha$-amino protective group of the incorporated amino acid to give the free $\alpha$-amino group. In the instance where the $\alpha$-amino protective group is a t-butyloxycarbonyl, trifluoroacetic acid in methylene chloride or chloroform, or hydrochloric acid in dioxane, is used to effect the deprotection. The deprotection is carried out at a temperature between about 0° C. and room temperature. Other standard cleaving reagents and conditions for removal of specific $\alpha$-amino protective groups may be used as described by E. Schröder and K. Lübke, in "The Peptides", Vol. 1, Academic Press, New York, 1965, pp. 72-75. After removal of the α-amino protective group from the last mentioned intermediate, the remaining α-amino protected amino acids (with side chain protection when required) are coupled stepwise in the desired order to obtain the corresponding protected peptide of formula 2 attached to the PAB resin. Each protected amino acid is introduced into the reaction system in one to four fold excess and the coupling is effected with a coupling agent (one to three fold excess) in a medium of methylene chloride, dimethylformamide, or mixtures of dimethylformamide and methylene chloride. In cases where incomplete coupling has occurred, the coupling procedure is repeated before removal of the α-amino protective group, prior to the coupling of the next protected amino acid. The success of the coupling reaction at each stage of the synthesis is monitored by the ninhydrin reaction as described by E. Kaiser et al., Anal. Biochem., 34, 595 (1970).

The preceding protected peptide of formula 2 thereafter is simultaneously cleaved from the resin and deprotected by treatment with liquid hydrogen fluoride to give the corresponding peptide of formula 1 in which Z is hydroxy.

When it is desired to prepare the C-terminal primary amide of formula 1 ($Z=NH_2$), the peptide can be prepared by the solid phase method using a benzhydrylamine resin and incorporating into the process the cleavage of the resulting resin-bound peptide and any required deprotection according to known procedures such as described by Stewart and Young, supra.

Alternatively, a convenient and practical method for preparing the preceding C-terminal primary amide, as well as the corresponding secondary and tertiary amides (i.e. peptides of formula 1 wherein Z is lower alkylamino or di(lower alkyl)amino, respectively), involves the solid phase method with a photolabile resin serving as the resin support. For instance, the stepwise coupling of the appropriate amino acid residues to 4-(2-chloropropionyl)phenoxyacetyl BHA resin, noted above, gives the protected peptide of formula 2 in which $Z^1$ is 4-(2-oxopropionyl)phenoxyacetyl BHA-resin. Subsequent photolysis of a suspension or solution of the latter peptide-resin (350 nm, 0° C., 6 to 24 hours) gives the corresponding protected peptide of formula 2 in which $Z^1$ is hydroxy. Coupling of the latter protected peptide with benzylamine or the appropriate lower alkylamine, e.g. methylamine or ethylamine, or the appropriate di(lower alkyl)amine, e.g. dimethylamine or ethylmethylamine, yields the respective protected peptide of formula 2 in which $Z^1$ is benzylamino, lower alkylamino or di(lower alkyl)amino. Deprotection of the latter protected peptide, for example with hydrofluoric acid, provides the corresponding C-terminal primary, secondary or tertiary amide of formula 1.

The terminal amino acylated derivatives of the peptides of formula 1, e.g. peptides of formula 1 wherein Y is (lower alkanoyl)-Phe or (lower alkanoyl)-Tyr, or Y is the decapeptide radical or fragment thereof wherein W is lower alkanoyl, are obtained from the corresponding free N-terminal amino peptide by treatment with a suitable acylating agent; for instance, the appropriate acid chloride or acid anhydride in the presence of a strong organic base, e.g. 1-oxobutylchloride with diisopropylethylamine or N-methylmorpholine. Alternatively, the terminal amino acylated derivatives are obtained by using the appropriate $N^\alpha$-acylated amino acid residue while preparing the peptide by conventional means. Again alternatively, the terminal amino acylated derivatives are obtained by coupling the corresponding free N-terminal amino peptide-resin (with side chain protection) with a molar equivalent of the appropriate lower alkanoic acid in the presence of a coupling agent; preferably (benzotriazol-1-yloxy)tris-(dimethylamino)phosphonium hexafluorophosphate, alone or in combination with 1-hydroxybenzotriazole, followed by conventional deprotection.

The peptide of formula 1 of this invention can be obtained in the form of therapeutically acceptable salts.

In the instance where a particular peptide has a residue which functions as a base, examples of such salts are those with organic acids, e.g. acetic, lactic, succinic, benzoic, salicylic, methanesulfonic or p-toluenesulfonic acid, as well as a polymeric acids such as tannic acid or carboxymethyl cellulose, and also salts with inorganic acids such as hydrohalic acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, example of such salts are those with the sodium, potassium or calcium cations, or with strong organic bases, for example triethylamine or N-methylmorpholine.

In general, the therapeutically acceptable salts of the peptides of formula 1 are biologically fully equivalent to the peptides themselves.

Biological aspects

The RR inhibiting and antineoplastic properties of the peptides of formula 1, or a therapeutically acceptable salt thereof, can be demonstrated by biochemical and biological procedures; for example, see H. L. Elford et al., Adv. Enz. Reg., 19, 151 (1981). In the examples hereinafter, the RR inhibitory effect of exemplified peptides of formula 1 on human RR is demonstrated in the "Inhibition of Human Ribonucleotide Reductase Assay", the procedure of which is based on similar assays reported by E. A. Cohen, J. Gen. Virol., 66, 733 (1985) and by Elford et al., supra.

Noteworthy is the finding that when the latter assay is repeated with other mammalian RR's and with RR's from bacterial and viral sources, a selective inhibition of mammalian RR is shown.

The ability of the peptides of formula 1 to selectively inhibit mammalian RR renders the peptides useful as agents for treating abnormal cell proliferation which occurs, for instance, in tumors (including both benign and malignant) and in psoriasis.

In the laboratory, the antineoplastic effect of the peptides can be demonstrated in tests with rodents having transplanted tumors. Survival time or tumor cell growth is used as the evaluation parameter. Examples of such transplantable tumors are lymphocytic leukemia, colon, mammary, melanocarcinoma and ependymoblastoma. The methods are described in various publications; for example, R. I. Geran et al, Cancer Chemotheraphy Report, Part 3, 3, 1-103 (1972) and references therein.

When the peptides of this invention, or their therapeutically acceptable salts, are employed as agents for combatting disease states associated with abnormal cell proliferation, they are administered topically or systemically to warm-blooded animals, e.g. humans, dogs, horses, in combination with pharmaceutical acceptable carriers, the proportion of which is determined by the solubility and chemical nature of the peptide, chosen route of administration and standard biological practice. For example, for the treatment of psoriasis the peptide of formula 1 can be employed topically. For topical application, the peptides may be formulated in the form of solutions, creams, or lotions in pharmaceutically acceptable vehicles containing 1.0–10 per cent, preferably 2 to 5 per cent of the agent, and may be administered topically to the infected area of the body.

For systemic administration, the peptides of formula 1 are administered by either intravenous, subcutaneous or intramuscular injection, in compositions with pharmaceutically acceptable vehicles or carriers. For administration by injection, it is preferred to use the peptides in solution in a sterile aqueous vehicle which may also contain other solutes such as buffer or preservatives as well as sufficient quantities of pharmaceutically acceptable salts or of glucose to make the solution isotonic.

Examples of suitable excipients or carriers are found in standards pharmaceutical texts, e.g. in "Remington's Pharmaceutical Sciences", 16th ed, Mack Publishing Company, Easton, Penn., USA, 1980.

The dosage of the peptides will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reched. In general, the peptides of this invention are most desirably administered at a concentration level that will generally afford effective results, without causing any harmful or deleterious side effects.

When used systemically as an antineoplastic or antitumor agent, the peptide of formula 1 is administered at a dose of 100 mcg to 1000 mcg per kilogram of body weight per day, although the aforementioned variations will occur. However, a dosage level that is in the range of from about 100 mcg to 500 mcg per kilogram of body weight per day is most desirably employed in order to achieve effective results.

The following examples illustrate further this invention. Solution percentages or ratios express volume to volume relationship, unless stated otherwise. Abbreviations used in the examples include Boc: t-butyloxycarbonyl; BOP: (benzotriazol-1-yloxy)tris(dimethylamino)phosphonium hexafluorophosphate; Bzl: benzyl; $CH_2Cl_2$: methylene chloride; Chxl: cyclohexyl; 2,6-DiClBzl: 2,6-dichlorobenzyl; DCC: N,N'-dicyclohexylcarbodiimide; DMF: dimethylformamide; HF: hydrofluoric acid; $Et_2O$: diethyl ether; EtOH: ethanol; HOBT: 1-hydroxy-benzotriazole; MeOH: methanol; TFA: trifluoroacetic acid.

EXAMPLE 1

Preparation of Boc-Phe-$CH_2$-PAB resin

Boc-Phe-OH (29.7 g, 112 mmol) and potassium fluoride (15.7 g, 252 mmol) were added to a mechanically stirred suspension of α-(4-chloromethylphenylacetamido)benzyl copoly(styrene-1% divinylbenzene) resin (50 g, 28 mmol, described by Giralt et al., supra) in DMF (600 ml). The mixture was stirred at 70° C. for 24 h, and then allowed to cool to ambient temperature. The solid was collected by filtration, washed successively with 100 ml portions of DMF, DMF-$H_2O$(1:1), $H_2O$, $H_2O$-dioxane(1:1), dioxane, MeOH, $CH_2Cl_2$ and EtOH, and dried under reduced pressure to give 54.4 g of the title compound. The phenylalanine content of the product was 0.54 mmol/g as determined by deprotection of an aliquot and picric acid tritration according to the method of B. F. Gisin, Anal. Chim. Acta, 58, 248 (1972).

EXAMPLE 2

Preparation of the N-acetyl-heptapeptide of the formula:

AcPhe-Thr-Leu-Asp-Ala-Asp-Phe-OH 

The title compound was synthetized by a modification of the solid-phase method of R. B. Merriffield, J. Amer. Chem. Soc., 85, 2149 (1963). Applying the method, the corresponding protected heptapeptide-resin having the correct sequence of amino acid residues was assembled by stepwise addition of the amino acids residues to Boc-Phe-$CH_2$-PAB resin, i.e. the title compound of Example 1. The following protocol was used: (a) Boc-deprotection: 30% TFA in $CH_2Cl_2$ (2 times, firstly for 5 min then for 25 min); (b) wash: $CH_2Cl_2$ (3 times for 2 min each); (c) wash: isopropanol (2 min); (d) neutralization: 5% diisopropylethylamine in $CH_2Cl_2$ (2 times for 2 min each); (e) amino acid coupling: achieved by the method of D. Hudson, J. Org. Chem., 53, 617 (1988) using the appropriate protected amino acid (2.1 molar equivalents per mmol of the Boc-Phe-$CH_2$-PAB resin) and BOP-HOBT (2.2 and 1.1 molar equivalents, respectively, per mmol of the Boc-Phe-$CH_2$-PAB resin) in the presence of N-methylmorpholine (6–8 molar equivalents providing pH 8 for the reaction mixture) in $CH_2Cl_2$ or DMF; the reaction time for coupling varied from 3 to 5 h; and (f) wash: $CH_2Cl_2$ or DMF (2 times for 2 min each. The Gln and Asn residues were coupled in DMF after activation of the corresponding Boc-amino acid with DCC-HOBT and removal by filtration of the N,N'-dicyclohexylurea formed during the activation process.

The Boc group gave $N^\alpha$ protection for all amino acids. Side chain protection was as follows: Bzl for Thr and Ser, Chxl for Asp and Glu, and 2,6-DiClBzl for Tyr. After each coupling, the completeness of the reaction was checked by the ninhydrin test, E. Kaiser et al., Anal. Biochem., 34, 595 (1970). The N-terminal acetylation was accomplished by coupling the free N-terminal amino protected peptide-resin with a molar equivalent of acetic acid using the BOP-HOBT method, or with acetic anhydride in the presence of diisopropylethylamine in $CH_2Cl_2$ or DMF.

On completion of the peptide sequence, the protected heptapeptide-resin was collected on a filter, washed with $CH_2Cl_2$ and EtOH and dried under reduced pressure over phosphorus pentoxide for 24 h to give the corresponding protected heptapeptide-resin (i.e. peptide-resin). The heptapeptide was cleaved from the peptide-resin by using HF (5 ml per g of peptide-resin) in the presence of distilled anisole (1 ml per g of peptide-resin) and ethanedithiol (0.2 ml per g of peptide-resin). The mixture was maintained at −20° C. for 40 min and then at 0°–5° C. for 40 min, with vigorous stirring. After evaporation of HF, the residue was triturated with $Et_2O$. The mixture was filtered through distomaceous earth (Celite ®). After washing with $Et_2O$, the filter cake was dried under reduced pressure. The residual solid was washed with several portions of 10% aqueous acetic acid, and then with 0.1M aqueous NH4OH (total volume: 40 ml per g of the peptide-resin). All the aqueous filtrates were mixed at 0° C. (pH 6) and lyophilized to afford a white solid residue.

Purification of the solid residue to greater than 95% homogeneity was accomplished by reversed phase HPLC with a Waters model 600 multisolvent delivery system (Waters, Milford, MA, USA) equipped with a UV detector and using a Whatman Partisil ® 100DS-3 C-18 column (2.2×50 cm²), 10 micron particle size. The elution was done with a gradient of acetonitrile in 0.1% aqueous TFA such as:

a) initial: 10% acetonitrile in 0.1% aqueous TFA for 20 min, b) followed by gradually increasing the concentration of acetonitrile to 20% over a period of 20 min, followed by gradually increasing the concentration to 40% acetonitrile over a period of 50 min.

Pure fractions, as determined by analytical HPLC, were pooled and lyophilized to afford the title heptapeptide as a trifluoroacetate salt. Analytical HPLC showed the product to be at least 95% homogeneous. Amino acid analysis: Phe, 2.00; Asp, 2.06; Thr, 0.95; Leu, 0.99; Ala, 1.00; FAB-MS, calcd: 869.38, found: 870 (M+H), 892 (M+Na), etc.

EXAMPLE 3

Inhibition of Human Ribonucleotide Reductase Assay

1) Preparation of extracts containing active RR (a) Cell line: Hela cells (ATCC CCL 2.2), human epitheloid carcinoma, cervix.

(b) Cell culture: Cells were incubated in a medium consisting of Iscove's Modified Dulbecco Medium, pH 7.2–7.4 (Gibco Canada Inc., Burlington, ON, Canada) supplemented with 10% by volume of fetal calf serum, heat inactivated (Gibco Canada Inc.), 1 millimolar (mM) of sodium pyruvate, 100 units/ml of penicillin G, 100 μg/ml of streptomycin and 2 mM of L-glutamine. The incubation was done in a 1 l spinner flask at 37° C. under a mixture of 5% $CO_2$ in air. Cell-containing media (75% of culture volume) was withdrawn semicontinuously at 24–48 h intervals. Fresh media was added each time to replace withdrawn media. Final cell density at harvest was $1-2 \times 10^6$ cells/ml.

(c) Preparation of cell extract containing human ribonucleotide reductase (hRR)

The harvested culture media obtained above was subjected to low speed centrifugation. The resulting cell pellet was processed according to the following steps. (All steps were performed at 4° C. unless noted otherwise.)

| Step | |
|---|---|
| 1) Wash Buffer | 100 mM $KH_2PO_4/K_2HPO_4$ in 0.9% (w/v) sodium chloride (pH 7.2). |
| 2) Storage | Cells frozen at −80° C. until extraction. |
| 3) Extraction Buffer | 25 mM N-2-hydroxyethyl-piperazine-N'-2-ethanesulfonic acid (HEPES) buffer (pH 7.6), 2 mM DL-dithiothreitol (DTT) and 1 mM $MgCl_2$. |
| 4) Cell Disruption | Cells in extraction buffer held for 30 min at 4° C. followed by 20 strokes on a Potter-Elvehjem Homogenizer (Kontes Glass Co., Vineland, NJ, USA). |
| 5) Centrifugation | 40,000 times gravity for 60 min; recover supernatant. |
| 6) Precipitation | A solution of 5% (w/v) streptomycin sulphate in 50 mM HEPES, 5 mM DTT and 5 mM $MgCl_2$ added dropwise to supernatant to give final concentration in mixture of 1% (w/v) of streptomycin sulfate. |
| 7) Centrifugation | 40,000 times gravity for 60 min; recover supernatant. |
| 8) Precipitation | Saturated $(NH_4)_2SO_4$ in HEPES/DTT/$MgCl_2$ buffer (see step 6) added slowly to supernatant to yield 50% saturated solution; solution agitated for 30 min. |
| 9) Centrifugation | 40,000 times gravity for 60 min.; recover pellet. |
| 10) Solubilization | Take up pellet in minimum volume of HEPES/DTT/$MgCl_2$ buffer (see step 6). |
| 11) Dialysis | 3-Cycle diafiltration (1h per cycle) carried out against HEPES/DTT/$MgCl_2$ buffer (see step 6) using a microconcentrator with a 10,000 MW cutoff (Centricon ® 10, Amicon, Danvers, MA, USA). |
| 12) Storage | Frozen at −80° C. |

2) Assay Protocol (a) Standard Reaction Mixture

| Component | Amount* |
|---|---|
| HEPES Buffer (pH 7.8) | 50 mM |
| Adenosine Triphosphate | 4 mM |
| DTT | 30 mM |
| $MgCl_2$ | 11.5 mM |
| NaF | 4 mM |
| Cytidine Diphosphate (CDP) | 0.054 mM |
| ($^{14}$C) CDP (DuPont Chemical Co. Lachine, QC, Canada) | 0.17 μCi/ml |
| Bacitracin | 1 mM |
| Test Compound | 1–250 μM |

*Final concentration of component in standard reaction mixture.

(b) Assay Procedure

The activity of RR was quantitated by following the conversion of radiolabeled cytidine diphosphate to radiolabeled deoxycytidine diphosphate, i.e. ($^{14}$C)CDP to ($^{14}$C)dCDP. The amount of cell extract utilized in the assay was that which gave a linear response between enzyme concentration and CDP conversion (ca. 200 μg of protein per assay).

After addition of the cell extract, the assay mixture was incubated at 37° C. for 30 min. The reaction was stopped by immersing the vessel containing the assay mixture in boiling water for 4 min. Nucleotides in the supernatant were then converted to nucleosides by the addition of excess *Crotalus adamenteus* snake venom (ca. 20 μl of a preparation of 40 mg/ml of the venom in an aqueous solution of 14 mM tris(hydroxymethyl)aminomethane (pH 8.8) and 46.5 mM $MgCl_2$), followed by incubating the resulting mixture for 60 min at 37° C. The enzymatic reaction was stopped by immersing the vessel containing the reaction mixture in boiling waster for 6 min. Thereafter, the mixture is centrifuged at 10,000 rpm on a clinical centrifuge for 5 min.

The resulting free nucleosides, cytidine (C) and deoxycytidine (dC), in the supernatant were separated by thin layer chromatography on polyethyleneimine-cellulose plates pretreated with boric acid. Elution of 5 μl samples was accomplished using a solution of ethanol/20 mM aqueous ammonium formate (1:1), pH 4.7. Quantitation of radiolabel migrating as C and dC was carried out using radioanalytical imaging equipment (AMBIS Systems Inc., San Diego, CA, USA). Substrate conversion was calculated as:

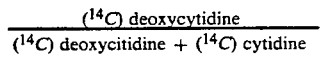

A unit of ribonucleotide reductase activity is defined as that amount which reduces one nmole of CDP/minute under the conditions described above. Activity was calculated from substrate conversion using the following relationship:

$$\left[\binom{\text{substrate}}{\text{conversion}}_{\text{(sample)}} - \binom{\text{substrate}}{\text{conversion}}_{\text{(blank)}}\right] \times$$

conversion factor = activity units

The conversion factor for the Hela assay was 0.108. Specific activity was expressed as units/mg of protein in the incubation mixture. In one embodiment, the specific activity of the Hela extract was found to be 0.2 units/mg.

The peptides of formula 1 were tested at a minimum of three concentrations. $IC_{50}$'s were estimated from graphs plotting the results for each peptide, the $IC_{50}$ being the concentration of the peptide in micromoles (μM) producing 50% of the maximal inhibition of the enzyme.

When the N-acetyl-heptapeptide of Example 2 having the formula AcPhe-Thr-Leu-Asp-Ala-Asp-Phe-OH was tested according to the assay of this example, an $IC_{50}$ of 38 μM was determined for the compound.

EXAMPLE 4

The following table of exemplified peptides of formula 1 further illustrates the invention. The peptides, prepared in a manner analogous to that described for the N-acetyl-heptapeptide of Example 2, are listed with their characterizing physical data and their $IC_{50}$ as determined by the inhibition of human RR assay of Example 3.

| Peptide | Amino Acid Analysis | FAB/MS Calcd (FW) | Found | $IC_{50}$ (μM) |
|---|---|---|---|---|
| H—Val—Ile—Ser—Asn—Ser—Thr—Glu—Asn—Ser—Phe—Thr—Leu—Asp—Ala—Asp—Phe—OH | Asp + Asn, 4.17; Thr, 1.97; Ser, 2.59; Glu, 0.97; Ala, 1.06; Val, 0.42; Ile, 0.40; Leu, 1.1; Phe, 2.14 | 1758.8 | 1759[1] | 49 |
| H—Asn—Ser—Thr—Glu—Asn—Ser—Phe—Thr—Leu—Asp—Ala—Asp—Phe—OH | Asp + Asn, 4.19; Thr, 1.94; Ser, 1.80; Glu, 1.0; Ala, 0.99; Leu, 1.01; Phe, 2.05 | 1459.6 | 1460[1] 1483[2] | 62 |
| H—Thr—Glu—Asn—Ser—Phe—Thr—Leu—Asp—Ala—Asp—Phe—OH | Asp + Asn, 3.08; Thr, 1.95; Ser, 0.92; Glu, 1.01; Ala, 1.0; Leu, 1.01; Phe, 2.03 | 1258.5 | 1259[1] 1281[2] | 95 |
| AcThr—Glu—Asn—Ser—Phe—Thr—Leu—Asp—Ala—Asp—Phe—OH | | 1301[1] 1300.6 | 1323[2] | 83 |
| Ac—Asn—Ser—Phe—Thr—Leu—Asp—Ala—Asp—Phe—OH | | 1070.5 | 1093[2] | 33 |

[1]Protonated parent ion (M + 1)
[2]Parent ion associated with Na+(M + 23)

The capacity of the peptides of formula 1, noted in Example 1 and listed above, to inhibit the enzymatic action of hamster RR was demonstrated by a variation of the RR assay of Example 2 wherein the cell extract of human RR is replaced by an extract of hamster RR. The latter extract was prepared according to the procedure of Cohen et al., supra, from hamster 600 H cells obtained from an overproducing strain of Chinese hamster lung cell line, selected for hydroxyurea resistance.

Other examples of peptides within the scope of this invention are listed hereinafter together with their $IC_{50}$ (shown in parenthesis) as determined in the inhibition of human RR assay:

AcPhe-Thr(OBzl)-Leu-Asp-Ala-Asp-Phe-OH(28),
AcPhe-Thr-Leu-Asp-Ala-N-Me-Asp-Phe-OH (46),
AcPhe-Thr-Phe-Asn-Glu-Asp-Phe-OH (150),
AcPhe-Thr-Leu-Asp-Ala-D-Asp-Phe-OH (280),
AcPhe-Thr-N-Me-Leu-Asp-Ala-Asp-Phe-OH (23),
AcPhe-N-Me-Val-Leu-Asp-Ala-Asp-Phe-OH (48),
AcPhe-Thr-Leu-Asp-D-Ala-Asp-Phe-OH (460),
AcPhe-Thr-Leu-D-Asp-Ala-Asp-Phe-OH (200),
AcPhe-Thr-Leu-Asp-Val-Asp-Phe-OH (39),
AcPhe-Thr-Leu-Gln-Ala-Asp-Phe-OH (120),
AcPhe-Thr-Leu-Asn-Ala-Asp-Phe-OH (31),
AcPhe-Thr-Leu-Asp-Ala-Asp-homoPhe-OH (58),
AcPhe-Thr-Leu-Asp-Glu-Asp-Phe-OH (28),
AcPhe-Thr-Leu-Asp(NMe₂)-Ala-Asp-Phe-OH (58),
AcPhe-Thr-Leu-Gly-Ala-Asp-Phe-OH (150),
AcPhe-Thr-Leu-Phe-Ala-Asp-Phe-OH (73),
H-Pro-Thr-Glu-Asn-Ser-Phe-Thr-Leu-Asp-Ala-Asp-Phe-OH (41),
H-Ser-Pro-Thr-Glu-Asn-Ser-Phe-Thr-Leu-Asp-Ala-Asp-Phe-OH (29), and
H-Ser-Ser-Pro-Thr-Glu-Asn-Ser-Phe-Thr-Leu-Asp-Ala-Asp-Phe-OH (26).

Still other examples of peptides within the scope of this invention include:

AcPhe-Ile-Leu-Asp-Ala-Asp-Phe-OH,
AcPhe-Ala-Leu-Asp-Ala-Asp-Phe-OH,
Ac-p-IPhe-Thr-Leu-Asp-Ala-Asp-Phe-OH,
H-Ser-Asn-Ser-Thr-Glu-Asn-Ser-Phe -Thr-Leu-Asp-Ala-Asp-Phe-OH,
AcSer-Ser-Pro-Thr-Glu-Asn-Ser-Phe -Thr-Leu-Asp-Ala-Asp-Phe-OH,
AcSer-Pro-Thr-Glu-Asn-Ser-Phe -Thr-Leu-Asp-Ala-Asp-Phe-OH,
AcPro-Thr-Glu-Asn-Ser-Phe -Thr-Leu-Asp-Ala-Asp-Phe-OH,
desamino-Phe-Thr-Leu-Asp-Ala-Asp-Phe-OH,
H-Met-Ser-Ser-Pro-Thr-Glu-Glu-Ser-Phe -Thr-Leu-Asp-Ala-Asp-Phe-OH,
desamino-Tyr-Ser-Ile-Glu-Ala-Asp-Phe-OH, AcAsn—Ser—Phe—Val—Val—Asp—Val—Asp—NHCHCOOH, 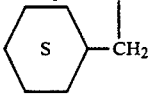

and

AcAsn—Ser—Phe—Thr—Leu—Asp—Ala—Asp—NHCHCOOH 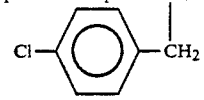

We claim:

1. A compound of formula 1

Y—R$^1$—R$^2$—R$^3$—R$^4$—R$^5$—R$^6$—Z     1 wherein
   R$^1$ is Thr, Thr(OBzl), Ser, Leu, Ile, Val, N-Me-Val or Ala,
   R$^2$ is Leu, D-Leu, N-Me-Leu, Ile, Val, Ala, Cha, N-Me-Cha or Phe,
   R$^3$ is Asp, D-Asp, N-Me-Asp, Asp(NMe$_2$), Asn, Glu, Gln, Leu, Ile, Val, Ala, Gly or Phe,
   R$^4$ is Ala, D-Ala, Val, Ile, Leu, Asp or Glu,
   R$^5$ is Asp, D-Asp, N-Me-Asp, Glu, D-Glu or N-Me-Glu,
   R$^6$ is Phe, homoPhe, or a divalent amino acid residue of formula X—CH$_2$CH(NH—)CO— wherein X is cyclohexyl, 4-(lower alkoxy)phenyl or 4-halophenyl;
   Y is Phe, desamino-Phe, (lower alkanoyl)-Phe, p-haloPhe, (lower alkanoyl)-p-haloPhe, Tyr, desamino-Tyr or (lower alkanoyl)-Tyr, or
   Y is the decapeptide radical W-Val-R$^7$-Ser-R$^8$-R$^9$-Thr-Glu-R$^{10}$-Ser-Phe wherein W is hydrogen or lower alkanoyl, and
   R$^7$ is Met or Ile,
   R$^8$ is Ser or Asn,
   R$^9$ is Pro or Ser, and
   R$^{10}$ is Asn, Gln, or
   Y is a fragment of said decapeptide radical wherein W, R$^7$, R$^8$, R$^9$ and R$^{10}$ are as defined hereinabove and wherein from one to nine of the amino acid residues (i.e. Val to Ser) may be deleted serially from the amino terminus of the decapeptide radical; and Z is hydroxy, amino, lower alkylamino or di(lower alkyl)amino; or a therapeutically acceptable salt thereof.

2. A peptide as recited in claim 1 wherein R$^1$ to R$^6$, inclusive, are as defined in claim 1, Y is Phe, desamino-Phe, AcPhe, Ac-p-haloPhe, Tyr, desamino-Tyr or Ac-Tyr, and Z is hydroxy or amino; or a therapeutically acceptable salt thereof.

3. A peptide as recited in claim 1 wherein R$^1$ to R$^6$, inclusive, are as defined in claim 1, Y is the decapeptide radical or a fragment of the decapeptide radical as defined in claim 1, and Z is hydroxy or amino; or a therapeutically acceptable salt thereof.

4. A peptide as recited in claim 2 wherein formula 1 wherein R$^1$ is Thr, Thr(OBzl), Ser, Ile, Val, N-Me-Val or Ala, R$^2$ is Leu, N-Me-Leu, Ile, Val or N-Me-Cha, R$^3$ is Asp, Asp(NMe$_2$), Asn, Glu, Gln or Ala, R$^4$ is Ala, Val, Asp or Glu, R$^5$ is Asp, N-Me-Asp or Glu, R$^6$ is Phe, homoPhe, or a divalent residue of formula X—CH$_2$CH(NH—)CO— wherein X is cyclohexyl, 4-methoxy phenyl or 4-fluorophenyl, Y is Phe, desamino-Phe, AcPhe, Ac-p-IPhe, Tyr, desamino-Tyr or Ac-Tyr, and Z is hydroxy or amino; or a therapeutically acceptable salt thereof.

5. A peptide as recited in claim 3 wherein R$^1$ is Thr, Thr(OBzl), Ser, Ile, Val, N-Me-Val or Ala, R$^2$ is Leu, N-Me-Leu, Ile, Val or N-Me-Cha, R$^3$ is Asp, Asp(NMe$_2$), Asn, Glu, Gln or Ala, R$^4$ is Ala, Val, Asp or Glu, R$^5$ is Asp, N-Me-Asp or Glu, R$^6$ is Phe, homoPhe, or a divalent residue of formula X—CH$_2$CH(NH—)-CO— wherein X is cyclohexyl, 4-methoxyphenyl or 4-fluorophenyl, Y is the decapeptide radical or a fragment of the decapeptide radical as defined in claim 3, and Z is as defined in claim 3, or a therapeutically acceptable salt thereof.

6. A peptide as recited in claim 4 wherein R$^1$ is as defined in claim 4, R$^2$ is Leu, N-Me-Leu or N-Me-Cha, R$^3$ is Asp, Asp(N-Me$_2$), Asn, Gln or Ala, R$^4$ is Ala or Glu, R$^5$ is Asp or N-Me-Asp, R$^6$ is Phe, Y is Phe, desamino-Phe or AcPhe, and Z is hydroxy; or a therapeutically acceptable salt thereof.

7. A peptide as recited in claim 5 wherein R$^1$ is as defined in claim 5, R$^2$ is Leu, N-Me-Leu or N-Me-Cha, R$^3$ is Asp, Asp(N-Me$_2$), Asn, Gln or Ala, R$^4$ is Ala or Glu, R$^5$ is Asp or N-Me-Asp, R$^6$ is Phe, Y is the decapeptide radical or one of the fragments thereof wherein W is hydrogen or acetyl, R$^7$ is Met or Ile, R$^8$ is Ser or Asn, R$^9$ is Pro or Ser, and R$^{10}$ is Asn, and Z is hydroxy; or a therapeutically acceptable salt thereof.

8. A peptide of formula 1 of claim 1 selected from the group of:
AcPhe-Thr-Leu-Asp-Ala-Asp-Phe-OH,
H-Val-Ile-Ser-Asn-Ser-Thr-Glu-Asn-Ser-Phe-Thr-Leu-Asp-Ala-Asp-Phe -OH,
H-Asn-Ser-Thr-Glu-Asn-Ser-Phe-Thr-Leu-Asp-Ala-Asp-Phe-OH,
H-Thr-Glu-Asn-Ser-Phe-Thr-Leu-Asp-Ala-Asp-Phe-OH,
AcThr-Glu-Asn-Ser-Phe-Thr-Leu-Asp-Ala-Asp-Phe-OH,
AcAsn-Ser-Phe-Thr-Leu-Asp-Ala-Asp-Phe-OH,
AcPhe-Thr(OBzl)-Leu-Asp-Ala-Asp-Phe-OH,
AcPhe-Thr-Leu-Asp-Ala-N-Me-Asp-Phe-OH,
AcPhe-Thr-Phe-Asn-Glu-Asp-Phe-OH,
AcPhe-Thr-Leu-Asp-Ala-D-Asp-Phe-OH,
AcPhe-Thr-N-Me-Leu-Asp-Ala-Asp-Phe-OH,
AcPhe-N-Me-Val-Leu-Asp-Ala-Asp-Phe-OH,
Ac-Phe-Thr-Leu-Asp-D-Ala-Asp-Phe-OH,
AcPhe-Thr-Leu-D-Asp-Ala-Asp-Phe-OH,
AcPhe-Thr-Leu-Asp-Val-Asp-Phe-OH,
AcPhe-Thr-Leu-Gln-Ala-Asp-Phe-OH, AcPhe-Thr-Leu-Asn-Ala-Asp-Phe-OH,
AcPhe-Thr-Leu-Asp-Ala-Asp-homoPhe-OH,
AcPhe-Thr-Leu-Asp-Glu-Asp-Phe-OH,
AcPhe-Thr-Leu-Asp(NMe$_2$)-Ala-Asp-Phe-OH,
AcPhe-Thr-Leu-Gly-Ala-Asp-Phe-OH,
AcPhe-Thr-Leu-Phe-Ala-Asp-Phe-OH,
H-Pro-Thr-Glu-Asn-Ser-Phe-Thr-Leu-Asp-Ala-Asp-Phe-OH,
H-Ser-Pro-Thr-Glu-Asn-Ser-Phe-Thr-Leu-Asp-Ala-Asp-Phe-OH,
H-Ser-Ser-Pro-Thr-Glu-Asn-Ser-Phe-Thr-Leu-Asp-Ala-Asp-Phe-OH.

9. A pharmaceutical composition comprising a peptide as recited in any of the claims 1 to 8, or a therapeutically acceptable salt thereof, and a pharmaceutically or veterinarily acceptable carrier.

10. A method for preventing or ameliorating abnormal cell proliferation in a mammal which comprises administering to the mammal an effective amount of a peptide as recited in claim 1, or a therapeutically acceptable salt thereof.

11. A method of inhibiting ribonucleotide reductase which comprises administering to a mammal carrying a tumor having a relatively high ribonucleotide reductase level of activity, an amount of a peptide as recited in claim 1, or a therapeutically acceptable salt thereof, effective to inhibit ribonucleotide reductase.

* * * * *